US007960155B1

(12) United States Patent
Hauer et al.

(10) Patent No.: US 7,960,155 B1
(45) Date of Patent: Jun. 14, 2011

(54) CYTOCHROME P450 MONOOXYGENASES AND THEIR USE FOR OXIDIZING ORGANIC COMPOUNDS

(75) Inventors: Bernhard Hauer, Fußgönheim (DE); Juergen Pleiss, Asperg (DE); Ulrich Schwaneberg, Waiblingen (DE); Jutta Schmitt, Stuttgart (DE); Markus Fischer, Ludwigsburg (DE); Rolf Schmid, Stuttgart (DE); Qing-shan Li, Kyoto (JP); Sabine Lutz-Wahl, Stuttgart (DE); Daniel Appel, Lauffen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 284 days.

(21) Appl. No.: 10/031,146

(22) PCT Filed: Jul. 27, 2000

(86) PCT No.: PCT/EP00/07253
§ 371 (c)(1),
(2), (4) Date: Jan. 17, 2002

(87) PCT Pub. No.: WO01/07630
PCT Pub. Date: Feb. 1, 2001

(30) Foreign Application Priority Data

| Jul. 27, 1999 | (DE) | 199 35 115 |
| Nov. 18, 1999 | (DE) | 199 55 605 |
| Mar. 22, 2000 | (DE) | 100 14 085 |

(51) Int. Cl.
| *C12N 9/02* | (2006.01) |
| *C12N 1/20* | (2006.01) |
| *C12N 15/00* | (2006.01) |
| *C12P 7/00* | (2006.01) |
| *C12P 21/04* | (2006.01) |
| *C12Q 1/26* | (2006.01) |
| *C12Q 1/00* | (2006.01) |
| *C12Q 1/68* | (2006.01) |
| *C07H 21/04* | (2006.01) |

(52) U.S. Cl. .......... 435/189; 435/4; 435/6; 435/25; 435/69.1; 435/71.1; 435/440; 435/252.3; 435/320.1; 435/132; 536/23.2

(58) Field of Classification Search ............ 435/190, 435/440, 320.1, 252.3, 325, 189, 4, 6, 18, 435/69.1, 71.1, 132; 536/23.2, 23.7
See application file for complete search history.

(56) References Cited

U.S. PATENT DOCUMENTS 5,834,297 A    11/1998    Oriel et al. ............ 435/252

FOREIGN PATENT DOCUMENTS

| GB | 2 294 692 | 5/1996 |
| GB | 195 07 546 | 9/1996 |
| GB | 2 306 485 | 5/1997 |
| WO | WO 00/09682 | 2/2000 |
| WO | WO 00/31273 | 6/2000 |

OTHER PUBLICATIONS

Branden et al. Introduction to Protein Structure, Garland Publishing Inc., New York, p. 247, 1991.*
Munro et al. "Regional Saturation Mutagenesis as an Approach to Identification of Substrate Specificity Determinants inCytochrom P450 Bm3" Biochemical Society Transactions vol. 21 (1993) pp. 4095.
Jones et al. "The oxidation of polychlorinated benzenes by geneticaly engineered cytochrome $P450_{cam}$; potential applications in biremediation" Chem. Commun. (2000) pp. 247-248.
Atkins et al. "Molecular Recognition in Cytochrome P-450; Alteration of Regioselective Alkane Hydroxylation via Protein Engineering" J. Am. Chem. Soc. vol. 111 (1989) pp. 2715-2717.
Sibbesen et al. "Putidaredoxin Reductase-Putidaredoxin-Cytochrome $P450_{cam}$ Triple Fusion Protein" Jnl. Biol. Chem. vol. 271 No. 37 (1996) pp. 22462-22469.
Gillam et al. "Formation of Indigo by Recombinant Mammalian Cytochrome $P450^1$" Biochemical and Biophysical Research Communiciations vol. 265 (1999) pp. 469-472.
Li et al. "Directed Evolution of the Fatty-Acid Hydroxylase P450 BM-3 into an Indole-Hydroxylating Catalyst" J. Chem. Eur. vol. 6 No. 9 (2000) pp. 1531-1536.
England et al. "The oxidation of naphthalene and pyrene by cytochrome $P450_{cam}$" FEBS Letters 424 (1998) pp. 271-274.
Yano, T., Oue, S., and Kagamiyama, H. (1998) Proc. Natl. Acad Sci. USA 95, 5511-5515.
Zhang, J.-H., Dawes, G., and Stemmer, W. P. C. (1997) Proc. Natl. Acad Sci. USA 94, 4504-4509.
Wan, L., Twitchett, M. B., Eltis, L. D., Mauk, A. G., and Smith, M. (1998) Proc. Natl. Acad Sci USA 95, 12825-12831.
Cronin, C. N. (1998) J. Biol. Chem 273, 24465-24469.
Wilks, H. M., Hart, K. W., Feeney, R., Dunn, C. R., Muirhead, H., Chia, W. N., Barstow, D. A., Atkinson, T., Clarke, A. R., Holbrook, I J. (1988) Science 242, 1541-1544.
Hedstrom, L., Szilagyi, L., Rutter, W. J. (1992) Science 255, 1249-1253.
Tucker, C. L., Hurley, J. H., Miller, T. R., and Hurley, I B. (1998) Proc. Natl. Acad Sci. USA 95, 5993-5997.
Quemeneur, E., Moutiez, J.-B. C., and Menez, A. (1998) Nature (London) 391, 301-303.
Marsden, A- F. A., Wilkinson, B., Cortes, J., Dunster, N. J., Staunton, I Leadlay, P. F. (1998) Science 279, 199-201.
Chen, R., Greer, A., and Dean, A. M. (1998) Proc. Natl. Acad. Sci. US4 95, 11666-11670.
Boddupalli, S. S., Estabrook, R. W. and Peterson, J. A. (1990) J Biol. Chem 265, 4233-4239.
Capdevila, J. H., Wie, S., Helvig, C., Falck, J. R., Belosludtsev, Y.,Truan, G., Graham-Lorence, S. E., and Peterson, J. A. (1996) J. Biol. Chem 271, 22663-22671.
Graham-Lorence, S., Truan, G., Peterson, J. A., Flack, J. R., WeL S., Helvig, C., Capdevilla, J. H. (1997) J. Biol. Chem 272, 1127-1135.
Li, H., Poulos, T. L. (1997) Nat. Structural Biol., 4, 140-146.

(Continued)

*Primary Examiner* — Yong D Pak
(74) *Attorney, Agent, or Firm* — Novak Druce + Quigg LLP

(57) ABSTRACT

The invention relates to novel cytochrome P450 monooxygenases comprising a modified substrate specificity, to nucleotide sequences which code therefor, to expression constructs and vectors containing these sequences, and to microorganisms transformed therewith. The invention also relates to methods for microbiologically oxidizing different organic substrates, such as methods for producing indigo and indirubin.

11 Claims, No Drawings

OTHER PUBLICATIONS

Ravichandran, K G., Sekhar, S., Boddupalli, S., Hasemann, C. A., Peterson, J. A., Deisenhofer, 1 (1993) Science 261, 731-736.

Modi S., Sutcliffe, M. J., Primrose, W. U., Lian, L.-Y., Roberts, G. C. K (1996) Nat. Structural Biol. 3, 414-417.

Oliver, C.F., ModL S., Primrose, W.U., Lian, L.Y. and Roberts, G.C.K (1997) Biochem. J. 327, 537-544.

Guengerich, F.G. (1991) J. Biol. Chem 266,10019-10022.

Cherry, J. R., Lamsa, M. H., Schneider, P., Vind, J., Svendsen, A-, Jones, A., and Pedersen, A. H. (1999) Nature Biotechnology 17, 379-384.

Schwaneberg, U., Schmidt-Dannert, C., Schmitt, J., and Schmid, R. D. (1999) Anal. Biochem. 269, 359-366.

Schwaneberg, U, Sprauer, AL, Schmidt-Dannert, C., and Schmid, R. D. J of Chromatogr. A 848, 149-159. 1999.

Oliver, C.F., Modi, S., Sutcliffe, M.J., Primrose, W.U., Lian, L.Y. and Roberts, G.C.K (1997) Biochemistry 36, 1567-1572.

Hart, S., Koch, KR., and Woods, D.R. (1992) J Gen. Microbiol. 138, 211-216.

Murdock, D., Ensley, B.D., Serdar, C. and Thalen, M. (1993) Bio/Technology 11, 381-385.

O'Connor, ICE., Dobson, A-W. and Hartmans, S. (1997) Appl. Environ. Microbiol. 63, 4287-4291.

Eaton, R. W. and Chapman, P. J. (1995) J Bacteriol. 177, 6983-6988.

\* cited by examiner

SEQUENCE LISTING

<160> NUMBER OF SEQ ID NOS: 9

<210> SEQ ID NO 1
<211> LENGTH: 3150
<212> TYPE: DNA
<213> ORGANISM: Bacillus megaterium
<220> FEATURE:
<221> NAME/KEY: CDS
<222> LOCATION: (4)..(3150)

<400> SEQUENCE: 1

```
atg aca att aaa gaa atg cct cag cca aaa acg ttt gga gag ctt aaa      48
    Thr Ile Lys Glu Met Pro Gln Pro Lys Thr Phe Gly Glu Leu Lys
      1               5                  10                  15 aat tta ccg tta tta aac aca gat aaa ccg gtt caa gct ttg atg aaa      96
Asn Leu Pro Leu Leu Asn Thr Asp Lys Pro Val Gln Ala Leu Met Lys
             20                  25                  30 att gcg gat gaa tta gga gaa atc ttt aaa ttc gag gcg cct ggt cgt     144
Ile Ala Asp Glu Leu Gly Glu Ile Phe Lys Phe Glu Ala Pro Gly Arg
         35                  40                  45 gta acg cgc tac tta tca agt cag cgt cta att aaa gaa gca tgc gat     192
Val Thr Arg Tyr Leu Ser Ser Gln Arg Leu Ile Lys Glu Ala Cys Asp
     50                  55                  60 gaa tca cgc ttt gat aaa aac tta agt caa gcg ctt aaa ttt gta cgt     240
Glu Ser Arg Phe Asp Lys Asn Leu Ser Gln Ala Leu Lys Phe Val Arg
 65                  70                  75 gat ttt gca gga gac ggg tta ttt aca agc tgg acg cat gaa aaa aat     288
Asp Phe Ala Gly Asp Gly Leu Phe Thr Ser Trp Thr His Glu Lys Asn
 80                  85                  90                  95 tgg aaa aaa gcg cat aat atc tta ctt cca agc ttc agt cag cag gca     336
Trp Lys Lys Ala His Asn Ile Leu Leu Pro Ser Phe Ser Gln Gln Ala
                100                 105                 110 atg aaa ggc tat cat gcg atg atg gtc gat atc gcc gtg cag ctt gtt     384
Met Lys Gly Tyr His Ala Met Met Val Asp Ile Ala Val Gln Leu Val
            115                 120                 125 caa aag tgg gag cgt cta aat gca gat gag cat att gaa gta ccg gaa     432
Gln Lys Trp Glu Arg Leu Asn Ala Asp Glu His Ile Glu Val Pro Glu
        130                 135                 140 gac atg aca cgt tta acg ctt gat aca att ggt ctt tgc ggc ttt aac     480
Asp Met Thr Arg Leu Thr Leu Asp Thr Ile Gly Leu Cys Gly Phe Asn
145                 150                 155 tat cgc ttt aac agc ttt tac cga gat cag cct cat cca ttt att aca     528
Tyr Arg Phe Asn Ser Phe Tyr Arg Asp Gln Pro His Pro Phe Ile Thr
160                 165                 170                 175 agt atg gtc cgt gca ctg gat gaa gca atg aac aag ctg cag cga gca     576
Ser Met Val Arg Ala Leu Asp Glu Ala Met Asn Lys Leu Gln Arg Ala
            180                 185                 190 aat cca gac gac cca gct tat gat gaa aac aag cgc cag ttt caa gaa     624
Asn Pro Asp Asp Pro Ala Tyr Asp Glu Asn Lys Arg Gln Phe Gln Glu
```

-continued

```
                195                 200                 205
gat atc aag gtg atg aac gac cta gta gat aaa att att gca gat cgc     672
Asp Ile Lys Val Met Asn Asp Leu Val Asp Lys Ile Ile Ala Asp Arg
        210                 215                 220 aaa gca agc ggt gaa caa agc gat gat tta tta acg cat atg cta aac     720
Lys Ala Ser Gly Glu Gln Ser Asp Asp Leu Leu Thr His Met Leu Asn
225                 230                 235 gga aaa gat cca gaa acg ggt gag ccg ctt gat gac gag aac att cgc     768
Gly Lys Asp Pro Glu Thr Gly Glu Pro Leu Asp Asp Glu Asn Ile Arg
240                 245                 250                 255 tat caa att att aca ttc tta att gcg gga cac gaa aca aca agt ggt     816
Tyr Gln Ile Ile Thr Phe Leu Ile Ala Gly His Glu Thr Thr Ser Gly
                260                 265                 270 ctt tta tca ttt gcg ctg tat ttc tta gtg aaa aat cca cat gta tta     864
Leu Leu Ser Phe Ala Leu Tyr Phe Leu Val Lys Asn Pro His Val Leu
            275                 280                 285 caa aaa gca gca gaa gaa gca gca cga gtt cta gta gat cct gtt cca     912
Gln Lys Ala Ala Glu Glu Ala Ala Arg Val Leu Val Asp Pro Val Pro
        290                 295                 300 agc tac aaa caa gtc aaa cag ctt aaa tat gtc ggc atg gtc tta aac     960
Ser Tyr Lys Gln Val Lys Gln Leu Lys Tyr Val Gly Met Val Leu Asn
305                 310                 315 gaa gcg ctg cgc tta tgg cca act gct cct gcg ttt tcc cta tat gca    1008
Glu Ala Leu Arg Leu Trp Pro Thr Ala Pro Ala Phe Ser Leu Tyr Ala
320                 325                 330                 335 aaa gaa gat acg gtg ctt gga gga gaa tat cct tta gaa aaa ggc gac    1056
Lys Glu Asp Thr Val Leu Gly Gly Glu Tyr Pro Leu Glu Lys Gly Asp
                340                 345                 350 gaa cta atg gtt ctg att cct cag ctt cac cgt gat aaa aca att tgg    1104
Glu Leu Met Val Leu Ile Pro Gln Leu His Arg Asp Lys Thr Ile Trp
            355                 360                 365 gga gac gat gtg gaa gag ttc cgt cca gag cgt ttt gaa aat cca agt    1152
Gly Asp Asp Val Glu Glu Phe Arg Pro Glu Arg Phe Glu Asn Pro Ser
        370                 375                 380 gcg att ccg cag cat gcg ttt aaa ccg ttt gga aac ggt cag cgt gcg    1200
Ala Ile Pro Gln His Ala Phe Lys Pro Phe Gly Asn Gly Gln Arg Ala
385                 390                 395 tgt atc ggt cag cag ttc gct ctt cat gaa gca acg ctg gta ctt ggt    1248
Cys Ile Gly Gln Gln Phe Ala Leu His Glu Ala Thr Leu Val Leu Gly
400                 405                 410                 415 atg atg cta aaa cac ttt gac ttt gaa gat cat aca aac tac gag ctg    1296
Met Met Leu Lys His Phe Asp Phe Glu Asp His Thr Asn Tyr Glu Leu
                420                 425                 430 gat att aaa gaa act tta acg tta aaa cct gaa ggc ttt gtg gta aaa    1344
Asp Ile Lys Glu Thr Leu Thr Leu Lys Pro Glu Gly Phe Val Val Lys
            435                 440                 445 gca aaa tcg aaa aaa att ccg ctt ggc ggt att cct tca cct agc act    1392
Ala Lys Ser Lys Lys Ile Pro Leu Gly Gly Ile Pro Ser Pro Ser Thr
        450                 455                 460 gaa cag tct gct aaa aaa gta cgc aaa aag gca gaa aac gct cat aat    1440
Glu Gln Ser Ala Lys Lys Val Arg Lys Lys Ala Glu Asn Ala His Asn
465                 470                 475 acg ccg ctg ctt gtg cta tac ggt tca aat atg gga aca gct gaa gga    1488
Thr Pro Leu Leu Val Leu Tyr Gly Ser Asn Met Gly Thr Ala Glu Gly
480                 485                 490                 495 acg gcg cgt gat tta gca gat att gca atg agc aaa gga ttt gca ccg    1536
Thr Ala Arg Asp Leu Ala Asp Ile Ala Met Ser Lys Gly Phe Ala Pro
                500                 505                 510 cag gtc gca acg ctt gat tca cac gcc gga aat ctt ccg cgc gaa gga    1584
Gln Val Ala Thr Leu Asp Ser His Ala Gly Asn Leu Pro Arg Glu Gly
```

-continued

```
            515                 520                 525
gct gta tta att gta acg gcg tct tat aac ggt cat ccg cct gat aac   1632
Ala Val Leu Ile Val Thr Ala Ser Tyr Asn Gly His Pro Pro Asp Asn
            530                 535                 540 gca aag caa ttt gtc gac tgg tta gac caa gcg tct gct gat gaa gta   1680
Ala Lys Gln Phe Val Asp Trp Leu Asp Gln Ala Ser Ala Asp Glu Val
            545                 550                 555 aaa ggc gtt cgc tac tcc gta ttt gga tgc ggc gat aaa aac tgg gct   1728
Lys Gly Val Arg Tyr Ser Val Phe Gly Cys Gly Asp Lys Asn Trp Ala
560                 565                 570                 575 act acg tat caa aaa gtg cct gct ttt atc gat gaa acg ctt gcc gct   1776
Thr Thr Tyr Gln Lys Val Pro Ala Phe Ile Asp Glu Thr Leu Ala Ala
            580                 585                 590 aaa ggg gca gaa aac atc gct gac cgc ggt gaa gca gat gca agc gac   1824
Lys Gly Ala Glu Asn Ile Ala Asp Arg Gly Glu Ala Asp Ala Ser Asp
            595                 600                 605 gac ttt gaa ggc aca tat gaa gaa tgg cgt gaa cat atg tgg agt gac   1872
Asp Phe Glu Gly Thr Tyr Glu Glu Trp Arg Glu His Met Trp Ser Asp
            610                 615                 620 gta gca gcc tac ttt aac ctc gac att gaa aac agt gaa gat aat aaa   1920
Val Ala Ala Tyr Phe Asn Leu Asp Ile Glu Asn Ser Glu Asp Asn Lys
            625                 630                 635 tct act ctt tca ctt caa ttt gtc gac agc gcc gcg gat atg ccg ctt   1968
Ser Thr Leu Ser Leu Gln Phe Val Asp Ser Ala Ala Asp Met Pro Leu
640                 645                 650                 655 gcg aaa atg cac ggt gcg ttt tca acg aac gtc gta gca agc aaa gaa   2016
Ala Lys Met His Gly Ala Phe Ser Thr Asn Val Val Ala Ser Lys Glu
            660                 665                 670 ctt caa cag cca ggc agt gca cga agc acg cga cat ctt gaa att gaa   2064
Leu Gln Gln Pro Gly Ser Ala Arg Ser Thr Arg His Leu Glu Ile Glu
            675                 680                 685 ctt cca aaa gaa gct tct tat caa gaa gga gat cat tta ggt gtt att   2112
Leu Pro Lys Glu Ala Ser Tyr Gln Glu Gly Asp His Leu Gly Val Ile
            690                 695                 700 cct cgc aac tat gaa gga ata gta aac cgt gta aca gca agg ttc ggc   2160
Pro Arg Asn Tyr Glu Gly Ile Val Asn Arg Val Thr Ala Arg Phe Gly
705                 710                 715 cta gat gca tca cag caa atc cgt ctg gaa gca gaa gaa aaa tta       2208
Leu Asp Ala Ser Gln Gln Ile Arg Leu Glu Ala Glu Glu Lys Leu
720                 725                 730                 735 gct cat ttg cca ctc gct aaa aca gta tcc gta gaa gag ctt ctg caa   2256
Ala His Leu Pro Leu Ala Lys Thr Val Ser Val Glu Glu Leu Leu Gln
            740                 745                 750 tac gtg gag ctt caa gat cct gtt acg cgc acg cag ctt cgc gca atg   2304
Tyr Val Glu Leu Gln Asp Pro Val Thr Arg Thr Gln Leu Arg Ala Met
            755                 760                 765 gct gct aaa acg gtc tgc ccg ccg cat aaa gta gag ctt gaa gcc ttg   2352
Ala Ala Lys Thr Val Cys Pro Pro His Lys Val Glu Leu Glu Ala Leu
            770                 775                 780 ctt gaa aag caa gcc tac aaa gaa caa gtg ctg gca aaa cgt tta aca   2400
Leu Glu Lys Gln Ala Tyr Lys Glu Gln Val Leu Ala Lys Arg Leu Thr
785                 790                 795 atg ctt gaa ctg ctt gaa aaa tac ccg gcg tgt gaa atg aaa ttc agc   2448
Met Leu Glu Leu Leu Glu Lys Tyr Pro Ala Cys Glu Met Lys Phe Ser
800                 805                 810                 815 gaa ttt atc gcc ctt ctg cca agc ata cgc ccg cgc tat tac tcg att   2496
Glu Phe Ile Ala Leu Leu Pro Ser Ile Arg Pro Arg Tyr Tyr Ser Ile
            820                 825                 830 tct tca tca cct cgt gtc gat gaa aaa caa gca agc atc acg gtc agc   2544
Ser Ser Ser Pro Arg Val Asp Glu Lys Gln Ala Ser Ile Thr Val Ser
```

-continued

```
                       835                 840                 845
gtt gtc tca gga gaa gcg tgg agc gga tat gga gaa tat aaa gga att    2592
Val Val Ser Gly Glu Ala Trp Ser Gly Tyr Gly Glu Tyr Lys Gly Ile
        850                 855                 860 gcg tcg aac tat ctt gcc gag ctg caa gaa gga gat acg att acg tgc    2640
Ala Ser Asn Tyr Leu Ala Glu Leu Gln Glu Gly Asp Thr Ile Thr Cys
865                 870                 875 ttt att tcc aca ccg cag tca gaa ttt acg ctg cca aaa gac cct gaa    2688
Phe Ile Ser Thr Pro Gln Ser Glu Phe Thr Leu Pro Lys Asp Pro Glu
880                 885                 890                 895 acg ccg ctt atc atg gtc gga ccg gga aca ggc gtc gcg ccg ttt aga    2736
Thr Pro Leu Ile Met Val Gly Pro Gly Thr Gly Val Ala Pro Phe Arg
                900                 905                 910 ggc ttt gtg cag gcg cgc aaa cag cta aaa gaa caa gga cag tca ctt    2784
Gly Phe Val Gln Ala Arg Lys Gln Leu Lys Glu Gln Gly Gln Ser Leu
            915                 920                 925 gga gaa gca cat tta tac ttc ggc tgc cgt tca cct cat gaa gac tat    2832
Gly Glu Ala His Leu Tyr Phe Gly Cys Arg Ser Pro His Glu Asp Tyr
        930                 935                 940 ctg tat caa gaa gag ctt gaa aac gcc caa agc gaa ggc atc att acg    2880
Leu Tyr Gln Glu Glu Leu Glu Asn Ala Gln Ser Glu Gly Ile Ile Thr
    945                 950                 955 ctt cat acc gct ttt tct cgc atg cca aat cag ccg aaa aca tac gtt    2928
Leu His Thr Ala Phe Ser Arg Met Pro Asn Gln Pro Lys Thr Tyr Val
960                 965                 970                 975 cag cac gta atg gaa caa gac ggc aag aaa ttg att gaa ctt ctt gat    2976
Gln His Val Met Glu Gln Asp Gly Lys Lys Leu Ile Glu Leu Leu Asp
                980                 985                 990 caa gga gcg cac ttc tat att tgc gga gac gga agc caa atg gca cct    3024
Gln Gly Ala His Phe Tyr Ile Cys Gly Asp Gly Ser Gln Met Ala Pro
            995                 1000                1005 gcc gtt gaa gca acg ctt atg aaa agc tat gct gac gtt cac caa gtg    3072
Ala Val Glu Ala Thr Leu Met Lys Ser Tyr Ala Asp Val His Gln Val
        1010                1015                1020 agt gaa gca gac gct cgc tta tgg ctg cag cag cta gaa gaa aaa ggc    3120
Ser Glu Ala Asp Ala Arg Leu Trp Leu Gln Gln Leu Glu Glu Lys Gly
    1025                1030                1035 cga tac gca aaa gac gtg tgg gct ggg taa                            3150
Arg Tyr Ala Lys Asp Val Trp Ala Gly
1040                1045
```

<210> SEQ ID NO 2
<211> LENGTH: 1048
<212> TYPE: PRT
<213> ORGANISM: Bacillus megaterium

<400> SEQUENCE: 2

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95
```

-continued

```
Lys Lys Ala His Asn Ile Leu Leu Pro Ser Phe Ser Gln Gln Ala Met
        100                 105                 110
Lys Gly Tyr His Ala Met Met Val Asp Ile Ala Val Gln Leu Val Gln
        115                 120                 125
Lys Trp Glu Arg Leu Asn Ala Asp Glu His Ile Glu Val Pro Glu Asp
130                 135                 140
Met Thr Arg Leu Thr Leu Asp Thr Ile Gly Leu Cys Gly Phe Asn Tyr
145                 150                 155                 160
Arg Phe Asn Ser Phe Tyr Arg Asp Gln Pro His Pro Phe Ile Thr Ser
                165                 170                 175
Met Val Arg Ala Leu Asp Glu Ala Met Asn Lys Leu Gln Arg Ala Asn
            180                 185                 190
Pro Asp Asp Pro Ala Tyr Asp Glu Asn Lys Arg Gln Phe Gln Glu Asp
            195                 200                 205
Ile Lys Val Met Asn Asp Leu Val Asp Lys Ile Ile Ala Asp Arg Lys
        210                 215                 220
Ala Ser Gly Glu Gln Ser Asp Asp Leu Leu Thr His Met Leu Asn Gly
225                 230                 235                 240
Lys Asp Pro Glu Thr Gly Glu Pro Leu Asp Asp Glu Asn Ile Arg Tyr
                245                 250                 255
Gln Ile Ile Thr Phe Leu Ile Ala Gly His Glu Thr Thr Ser Gly Leu
            260                 265                 270
Leu Ser Phe Ala Leu Tyr Phe Leu Val Lys Asn Pro His Val Leu Gln
        275                 280                 285
Lys Ala Ala Glu Glu Ala Ala Arg Val Leu Val Asp Pro Val Pro Ser
        290                 295                 300
Tyr Lys Gln Val Lys Gln Leu Lys Tyr Val Gly Met Val Leu Asn Glu
305                 310                 315                 320
Ala Leu Arg Leu Trp Pro Thr Ala Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Leu Met Val Leu Ile Pro Gln Leu His Arg Asp Lys Thr Ile Trp Gly
        355                 360                 365
Asp Asp Val Glu Glu Phe Arg Pro Glu Arg Phe Glu Asn Pro Ser Ala
370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Gly Phe Val Val Lys Ala
        435                 440                 445
Lys Ser Lys Lys Ile Pro Leu Gly Gly Ile Pro Ser Pro Ser Thr Glu
        450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
        515                 520                 525
```

```
Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
```

```
                        945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
            980                 985                 990
Gly Ala His Phe Tyr Ile Cys Gly Asp Gly Ser Gln Met Ala Pro Ala
        995                 1000                1005
Val Glu Ala Thr Leu Met Lys Ser Tyr Ala Asp Val His Gln Val Ser
    1010                1015                1020
Glu Ala Asp Ala Arg Leu Trp Leu Gln Gln Leu Glu Glu Lys Gly Arg
1025                1030                1035                1040
Tyr Ala Lys Asp Val Trp Ala Gly
            1045

<210> SEQ ID NO 3
<211> LENGTH: 30
<212> TYPE: DNA
<213> ORGANISM: Synthetic sequence
<220> FEATURE:
<221> NAME/KEY: unsure
<222> LOCATION: 1..30
<223> OTHER INFORMATION: n is g, a, t or c.
<220> FEATURE:
<223> OTHER INFORMATION: Description of the synthetic sequence: PCR
      primer

<400> SEQUENCE: 3
gcaggagacg ggttgnnnac aagctggacg                                     30

<210> SEQ ID NO 4
<211> LENGTH: 30
<212> TYPE: DNA
<213> ORGANISM: Synthetic sequence
<220> FEATURE:
<221> NAME/KEY: unsure
<222> LOCATION: 1..30
<223> OTHER INFORMATION: n is g, a, t or c.
<223> OTHER INFORMATION: Description of the synthetic sequence: PCR
      primer

<400> SEQUENCE: 4
cgtccagctt gtnnncaacc cgtctcctgc                                     30

<210> SEQ ID NO 5
<211> LENGTH: 34
<212> TYPE: DNA
<213> ORGANISM: Synthetic sequence
<220> FEATURE:
<221> NAME/KEY: unsure
<222> LOCATION: 1..34
<223> OTHER INFORMATION: n is g, a, t or c.
<223> OTHER INFORMATION: Description of the synthetic sequence: PCR
      primer

<400> SEQUENCE: 5
gaagcaatga acaagnnnca gcgagcaaat ccag                                34

<210> SEQ ID NO 6
<211> LENGTH: 30
<212> TYPE: DNA
<213> ORGANISM: Synthetic sequence
<220> FEATURE:
<221> NAME/KEY: unsure
<222> LOCATION: 1..30
<223> OTHER INFORMATION: n is g, a, t or c.
<223> OTHER INFORMATION: Description of the synthetic sequence: PCR
      primer
```

-continued

<210> SEQ ID NO 7
<211> LENGTH: 41
<212> TYPE: DNA
<213> ORGANISM: Synthetic sequence
<220> FEATURE:
<221> NAME/KEY: unsure
<222> LOCATION: 1..41
<223> OTHER INFORMATION: n is g, a, t or c.
<223> OTHER INFORMATION: Description of the synthetic sequence: PCR
      primer

<400> SEQUENCE: 7
gctttgataa aaacttaaag tcaannncttt aaatttgtac g                    41

<210> SEQ ID NO 8
<211> LENGTH: 40
<212> TYPE: DNA
<213> ORGANISM: Synthetic sequence
<220> FEATURE:
<221> NAME/KEY: unsure
<222> LOCATION: 1..40
<223> OTHER INFORMATION: n is g, a, t or c.
<223> OTHER INFORMATION: Description of the synthetic sequence: PCR
      primer

<400> SEQUENCE: 8
cgtacaaatt taagnnnttg acttaagttt ttatcaaagc                       40

<210> SEQ ID NO 9
<211> LENGTH: 1049
<212> TYPE: PRT
<213> ORGANISM: Bacillus megaterium

<400> SEQUENCE: 9

Met Thr Ile Lys Glu Met Pro Gln Pro Lys Thr Phe Gly Glu Leu Lys
 1               5                  10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

```
Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ala Asp Arg
        210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
        275                 280                 285

Gln Lys Ala Ala Glu Ala Ala Arg Val Leu Val Asp Pro Val Pro
        290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Leu Met Val Leu Ile Pro Gln Leu His Arg Asp Lys Thr Ile Trp
                355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
                515                 520                 525

Ala Val Leu Ile Val Thr Ala Ser Tyr Asn Gly His Pro Pro Asp Asn
                530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
                595                 600                 605

Asp Phe Glu Gly Thr Tyr Glu Glu Trp Arg Glu His Met Trp Ser Asp
```

```
              610                 615                 620
Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
                675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
                740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
                850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
                995                 1000                1005

Ala Val Glu Ala Thr Leu Met Lys Ser Tyr Ala Asp Val His Gln Val
     1010                1015                1020

Ser Glu Ala Asp Ala Arg Leu Trp Leu Gln Gln Leu Glu Glu Lys Gly
1025                1030                1035                1040
```

-continued

```
Arg Tyr Ala Lys Asp Val Trp Ala Gly
        1045
```

CYTOCHROME P450 MONOOXYGENASES AND THEIR USE FOR OXIDIZING ORGANIC COMPOUNDS

The present invention relates to novel cytochrome P450 monooxygenases with modified substrate specificity which are capable of the oxidation of organic substrates, for example N-heterocyclic aromatic compounds, nucleotide sequences coding therefor, expression constructs and vectors comprising these sequences, microorganisms transformed therewith, processes for the microbiological oxidation of various organic substrates, such as N-heterocyclic aromatic compounds and in particular processes for the preparation of indigo and indirubin.

Enzymes having novel functions and properties can be prepared either by screening of natural samples or by protein engineering of known enzymes. Under certain circumstances, the last-mentioned method can be the more suitable to induce characteristics whose generation by the natural selection route is improbable. Despite numerous attempts at the engineering of enzymes, up to now there are only a few successful studies for promoting the catalytic activity of enzyme mutants with respect to a certain substrate (1-10). In these known cases, the substrates are structurally closely related to the native substrate of the respective enzyme. As yet, there are no reports on the successful engineering of enzymes which, after modification, catalyze the reaction of a compound which structurally is completely different from the native substrate of the enzyme.

The cytochrome P450 monooxygenase isolatable from the bacterium *Bacillus megaterium* usually catalyzes the subterminal hydroxylation of long-chain, saturated acids and the corresponding amides and alcohols thereof or the epoxidation of unsaturated long-chain fatty acids or saturated fatty acids of medium chain length (11-13). The optimal chain length of saturated fatty acids is 14 to 16 carbon atoms. Fatty acids having a chain length of less than 12 are not hydroxylated (11).

The structure of the heme domain of P450 BM-3 was determined by X-ray structural analysis (14-16). The substrate binding site is present in the form of a long tunnel-like opening which extends from the surface of the molecule as far as the heme molecule and is almost exclusively bordered by hydrophobic amino acid residues. The only charged residues on the surface of the heme domain are the residues Arg47 and Tyr51. It is assumed that these are involved in the binding of the carboxylate group of the substrate by formation of a hydrogen bond (14). The mutation of Arg47 to Glu brings about inactivation of the enzyme for arachidonic acid (13), but increases its activity compared with $C_{12}$-$C_{14}$-alkyltrimethylammonium compounds (17). Substrate utilization for aromatic compounds, in particular mono-, bi- or polynuclear, if desired heterocyclic, aromatics, alkanes, alkenes, cycloalkanes and cycloalkenes, has not been described for this enzyme. Until now, it was therefore assumed in specialist circles that substrates other than the organic substrates hitherto described, for example indole, on account of the clear structural differences from the native substrates of P450 BM-3, in particular on account of the absence of functional groups which could bind to the abovementioned residues in the substrate pocket, are not a substrate.

It is an object of the present invention to make available novel cytochrome P450 monooxygenases having modified substrate specificity or modified substrate profile. In particular, monooxygenase mutants are to be provided which, in comparison with the nonmutated wild-type enzyme, are enzymatically active with structurally clearly different substrates.

Compared to the wild-type enzyme, a "modified substrate profile" can be observed for the mutants according to the invention. In particular, for the mutant in question, an improvement in reactivity is observed, for example an increase of the specific activity (expressed as nmol of converted substrate/minute/nmol of P450 enzyme) and/or of at least one kinetic parameter selected from the group consisting of Kcat, Km and Kcat/Km (for example by at least 1%, such as 10 to 1000%, 10 to 500% or 10 to 100%) in the conversion of at least one of the oxidizable compounds defined in groups a) to d). The oxidation reaction according to the invention comprises the enzyme-catalyzed oxygenation of at least one exogenous (i.e. added to the reaction medium) or endogenous (i.e. already present in the reaction medium) organic substrate. In particular, the oxidation reaction according to the invention comprises a mono- and/or polyhydroxylation, for example a mono- and/or dihydroxylation, at an aliphatic or aromatic C—H group, or an epoxidation at a C=C group which is preferably non-aromatic. Also possible are combinations of the above reactions. Moreover, the immediate reaction product can be converted further in the context of a non-enzymatic subsequent or side reaction. Such combinations of enzymatic and non-enzymatic processes likewise form part of the subject-matter of the present invention.

We have found that the above object is surprisingly achieved by means of novel cytochrome P450 monooxygenases which, for example, are capable of the oxidation of N-heterocyclic bi- or polynuclear aromatic compounds.

In particular, the invention relates to those monooxygenases whose substrate-binding region is capable by means of site-specific mutagenesis of the functional uptake of novel, for example N-heterocyclic substrates.

In a preferred embodiment of the invention, the novel monooxygenases are soluble, i.e. existent in non membrane-bound form, and enzymatically active in this form.

The monooxygenases according to the invention are preferably derived from cytochrome P450 monooxygenases of bacterial origin, as derived, in particular, from cytochrome P450 monooxygenase BM-3 from *Bacillus megaterium* having an amino acid sequence according to SEQ ID NO:2, which has at least one functional mutation, i.e. promoting the oxidation of novel organic substrates (cf. in particular the groups a) to d) of compounds as defined below), for example N-heterocyclic mono-, bi- or polynuclear aromatic compounds, in one of the amino acid sequence regions 172-224 (F/G loop region), 39-43 (β-strand 1), 48-52 (β-strand 2), 67-70 (β-strand 3), 330-335 (β-strand 5), 352-356 (β-strand 8), 73-82 (helix 5) and 86-88 (helix 6).

The cytochrome P450 monooxygenase mutants provided according to the invention are preferably capable of at least one of the following reactions:

a) oxidation of unsubstituted or substituted N-, O- or S-heterocyclic mono-, bi- or polynuclear aromatic compounds;
b) oxidation of unsubstituted or substituted mono- or polynuclear aromatics;
c) oxidation of straight-chain or branched alkanes and alkenes; and
d) oxidation of unsubstituted or substituted cycloalkanes and cycloalkenes.

Preferred monooxygenase mutants have at least one functional mutation, in particular amino acid substitution, in at least one of the sequence regions 73-82, 86-88 and 172-224. Thus, for example, Phe87 can be replaced by an amino acid having an aliphatic side chain, such as Ala, Val, Leu, in particular Val; Leu188 can be replaced by an amino acid having an amide side chain, such as Asn or, in particular, Gln; and Ala74 can be replaced by another amino acid having an aliphatic side chain, such as Val and, in particular, Gly.

Particularly preferred monooxygenase mutants of this type are those which have at least one of the following mono- or polyamino acid substitutions:
1) Phe87Val;
2) Phe87Val, Leu188Gln; or
3) Phe87Val, Leu188Gln, Ala74Gly;
and functional equivalents thereof. The number indicates the position of the mutation; the original amino acid is indicated before the number and the newly introduced amino acid after the number.

In this context, "functional equivalents" or analogs of the mutants which are disclosed specifically are mutants differing therefrom which furthermore have the desired substrate specificity with respect to at least one of the oxidation reactions a) to d) described above, i.e., for example, for heterocyclic aromatics and which hydroxylate, for example, indole, or furthermore exhibit the desired "modified substrate profile" with respect to the wild-type enzyme.

"Functional equivalents" are also to be understood as meaning in accordance with the invention mutants which exhibit, in at least one of the abovementioned sequence positions, an amino acid substitution other than the one mentioned specifically, but still lead to a mutant which, like the mutant which has been mentioned specifically, show a "modified substrate profile" with respect to the wild-type enzyme and catalyze at least one of the abovementioned oxidation reactions. Functional equivalence exists in particular also in the case where the modifications in the substrate profile correspond qualitatively, i.e. where, for example, the same substrates are converted, but at different rates.

"Functional equivalents" naturally also encompass P450 monooxygenase mutants which, like the P450 BM3 mutants which have been mentioned specifically, can be obtained by mutating P450 enzymes from other organisms. For example, regions of homologous sequence regions can be identified by sequence comparison. Following the principles of what has been set out specifically in the invention, the modern methods of molecular modeling then allow equivalent mutations to be carried out which affect the reaction pattern.

"Functional equivalents" also encompass the mutants which can be obtained by one or more additional amino acid additions, substitutions, deletions and/or inversions, it being possible for the abovementioned additional modifications to occur in any sequence position as long as they give rise to a mutant with a modified substrate profile in the above sense.

Substrates of group a) which can be oxidized according to the invention are unsubstituted or substituted heterocyclic mono-, bi- or polynuclear aromatic compounds; in particular oxidizable or hydroxylatable N-, O- or S-heterocyclic mono-, bi- or polynuclear aromatic compounds. They include preferably two or three, in particular two, 4- to 7-membered, in particular 6- or 5-membered, fused rings, where at least one, preferably all, rings have aromatic character and where at least one of the aromatic rings carries one to three, preferably one, N-, O- or S-heteroatom in the ring. The total ring structure may contain one or two further identical or different heteroatoms. The aromatic compounds may furthermore carry 1 to 5 substituents at the ring carbon or heteroatoms. Examples of suitable substituents are $C_1$- to $C_4$-alkyl, such as methyl, ethyl, n- or isopropyl, n-, iso- or t-butyl, or $C_2$- to $C_4$-alkenyl, such as ethenyl, 1-propenyl, 2-propenyl, 1-butenyl, 2-butenyl or 3-butenyl, hydroxyl and halogen, such as F, Cl and Br. The alkyl or alkenyl substituents mentioned may also have a keto or aldehyde group; examples being propan-2-on-3-yl, butan-2-on-4-yl, 3-buten-2-on-4-yl. Non-limiting examples of suitable heterocyclic substrates are, in particular, binuclear heterocycles, such as indole, N-methyl-indole, and the substituted analogs thereof which carry one to three of the above-defined substituents on carbon atoms, for example 5-chloro- or 5-bromoindole; and also quinoline and quinoline derivatives, for example 8-methylquinoline, 6-methyl-quinoline and quinaldine; and benzothiophene, and the substituted analogs thereof which carry one to three of the above-defined substituents on carbon atoms. Moreover, trinuclear heteroaromatics, such as acridine and the substituted analogs thereof which carry one to three of the above-defined substituents on carbon atoms, may be mentioned.

Substrates of group b) which are oxidizable according to the invention are unsubstituted or substituted mono- or polynuclear, in particular mono- or binuclear, aromatics, such as benzene and naphthalene. The aromatic compounds may be unsubstituted or mono- or polysubstituted and, for example, carry 1 to 5 substituents on the ring carbon atoms. Examples of suitable substituents are $C_1$- to $C_4$-alkyl, such as methyl, ethyl, n- or isopropyl or n-, iso- or t-butyl, or $C_2$- to $C_4$-alkenyl, such as ethenyl, 1-propenyl, 2-propenyl, 1-butenyl, 2-butenyl or 3-butenyl, hydroxyl and halogen, such as F, Cl and Br. The alkyl or alkenyl substituents mentioned may also have a keto or aldehyde group; Examples being propan-2-on-3-yl, butan-2-on-4-yl, 3-buten-2-on-4-yl. The aromatic may be fused with a four- to seven-membered non-aromatic ring. The non-aromatic ring may have one or two C=C double bonds, be mono- or polysubstituted by the abovementioned substituents and may carry one or two hetero ring atoms. Examples of particularly suitable aromatics are mononuclear aromatics, such as cumene, and binuclear substrates, such as indene and naphthalene, and substituted analogs thereof which carry one to three of the above-defined substituents on carbon atoms.

Substrates of group c) which can be oxidized according to the invention are straight-chain or branched alkanes or alkenes having 4 to 15, preferably 6 to 12, carbon atoms. Examples which may be mentioned are n-butane, n-pentane, n-hexane, n-heptane, n-octane, n-nonane, n-decane, n-undecane and n-dodecane, and the analogs of these compounds which are branched once or more than once, for example analogous compounds having 1 to 3 methyl side groups; or mono- or polyunsaturated, for example mono-unsaturated, analogs of the abovementioned alkanes.

Substrates of group d) which can be oxidized according to the invention are unsubstituted or substituted cycloalkanes and cycloalkenes having 4 to 8 ring carbon atoms. Examples of these are cyclopentane, cyclopentene, cyclohexane, cyclohexene, cycloheptane and cycloheptene. The ring structure may carry one or more, for example 1 to 5, substituents according to the above definition for compounds of groups a) and b). Nonlimiting examples are ionones, such as α-, β- and γ-ionone, and the corresponding methyl ionones and isomethyl ionones. Particular preference is given to α- and β-ionone.

The invention also relates to nucleic acid sequences coding for one of the monooxygenases according to the invention. Preferred nucleic acid sequences are derived from SEQ ID NO:1, which have at least one nucleotide substitution which leads to one of the functional amino acid mutations described above. The invention moreover relates to functional analogs of the nucleic acids obtained by addition, substitution, insertion and/or deletion of individual or multiple nucleotides, which furthermore code for a monooxygenase having the desired substrate specificity, for example having indole-oxidizing activity.

The invention also encompasses those nucleic acid sequences which comprise so-called silent mutations or which are modified in comparison with a specifically mentioned sequence in accordance with the codon usage of a specific origin or host organism, and naturally occurring variants of such nucleic acid sequences. The invention also encompasses modifications of the nucleic acid sequences obtained by degeneration of the genetic code (i.e. without any changes in the corresponding amino acid sequence) or conservative nucleotide substitution (i.e. the corresponding amino acid is replaced by another amino acid of the same charge, size, polarity and/or solubility), and sequences modified by nucleotide addition, insertion, inversion or deletion, which sequences encode a monooxygenase according to the invention having a "modified substrate profile", and the corresponding complementary sequences.

The invention furthermore relates to expression constructs comprising a nucleic acid sequence encoding a mutant according to the invention under the genetic control of regulatory nucleic acid sequences; and vectors comprising at least one of these expression constructs.

Preferably, the constructs according to the invention encompass a promoter 5'-upstream of the encoding sequence in question and a terminator sequence 3'-downstream, and, optionally, further customary regulatory elements, and, in each case operatively linked with the encoding sequence. Operative linkage is to be understood as meaning the sequential arrangement of promoter, encoding sequence, terminator and, if appropriate, other regulatory elements in such a manner that each of the regulatory elements can fulfill its intended function on expression of the encoding sequence. Examples of operatively linkable sequences are targeting sequences, or else translation enhancers, enhancers, polyadenylation signals and the like. Further regulatory elements encompass selectable markers, amplification signals, replication origins and the like.

In addition to the artificial regulatory sequences, the natural regulatory sequence can still be present upstream of the actual structural gene. If desired, this natural regulation may be switched off by genetic modification, and the expression of the genes may be enhanced or lowered. However, the gene construct may also be simpler in construction, i.e. no additional regulatory signals are inserted upstream of the structural gene and the natural promoter with its regulation is not removed. Instead, the natural regulatory sequence is mutated in such a way that regulation no longer takes place and the gene expression is increased or reduced. One or more copies of the nucleic acid sequences may be present in the gene construct.

Examples of suitable promoters are: cos, tac, trp, tet, trp-tet, lpp, lac, lpp-lac, lacIq, T7, T5, T3, gal, trc, ara, SP6, 1-PR or 1-PL promoter, which are advantageously employed in Gram-negative bacteria; and Gram-positive promoters amy and SPO2, the yeast promoters ADC1, MFa, Ac, P-60, CYC1, GAPDH or the plant promoters CaMV/35S, SSU, OCS, lib4, usp, STLS1, B33, nos or the ubiquitin or phaseolin promoter. Particular preference is given to using inducible promoters, for example light- and in particular temperature-inducible promoters, such as the $P_rP_1$ promoter.

In principle, all natural promoters with their regulatory sequences can be used. In addition, synthetic promoters may also be used in an advantageous fashion.

The abovementioned regulatory sequences are intended to allow the targeted expression of the nucleic acid sequences and of protein expression. Depending on the host organism, this may mean, for example, that the gene is expressed or overexpressed only after induction has taken place, or that it is expressed and/or overexpressed immediately.

The regulatory sequences or factors can preferably have a positive effect on expression and in this manner increase or reduce the latter. Thus, an enhancement of the regulatory elements may advantageously take place at the transcriptional level by using strong transcription signals such as promoters and/or "enhancers". In addition, translation may also be enhanced by improving, for example, mRNA stability.

An expression cassette is generated by fusing a suitable promoter with a suitable monooxygenase nucleotide sequence and a terminator signal or polyadenylation signal. To this end, customary recombination and cloning techniques are used as they are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which allows optimal gene expression in the host. Vectors are well known to the skilled worker and can be found, for example, in "Cloning Vectors" (Pouwels P. H. et al., Ed., Elsevier, Amsterdam-New York-Oxford, 1985). Vectors are to be understood as meaning not only plasmids, but all other vectors known to the skilled worker such as, for example, phages, viruses, such as SV40, CMV, baculovirus and adenovirus, transposons, IS elements, phasmids, cosmids, and linear or circular DNA. These vectors can be replicated autonomously in the host organism or chromosomally.

The vectors according to the invention allow the generation of recombinant microorganisms which are transformed, for example, with at least one vector according to the invention and which can be employed for producing the mutants. The above-described recombinant constructs according to the invention are advantageously introduced into a suitable host system and expressed. It is preferred to use usual cloning and transfection methods known to the skilled worker in order to bring about expression of the abovementioned nucleic acids in the expression system in question. Suitable systems are described, for example, in current protocols in molecular biology, F. Ausubel et al., Ed., Wiley Interscience, New York 1997.

Suitable host organisms are, in principle, all organisms which allow expression of the nucleic acids according to the invention, their allelic variants, and their functional equivalents or derivatives. Host organisms are to be understood as meaning, for example, bacteria, fungi, yeasts or plant or animal cells. Preferred organisms are bacteria such as those of the genera *Escherichia*, such as, for example, *Escherichia coli, Streptomyces, Bacillus* or *Pseudomonas*, eukaryotic microorganisms such as *Saccharomyces cerevisiae, Aspergillus*, and higher eukaryotic cells from animals or plants, for example Sf9 or CHO cells.

If desired, expression of the gene product may also be brought about in transgenic organisms such as transgenic animals such as, in particular, mice, sheep, or transgenic plants. The transgenic organisms may also be knock-out animals or plants in which the corresponding endogenous gene has been eliminated, such as, for example, by mutation or partial or complete deletion.

Successfully transformed organisms can be selected by marker genes which are likewise contained in the vector or in the expression cassette. Examples of such marker genes are genes for resistance to antibiotics and for enzymes which catalyze a color reaction, which causes staining of the transformed cell. These transformed cells can then be selected using automatic cell selection. Microorganisms which have been transformed successfully with a vector and which carry an appropriate gene for resistance to antibiotics (for example G418 or hygromycin) can be selected by using appropriate antibiotics-containing media or substrates. Marker proteins which are presented on the cell surface can be used for selection by affinity chromatography.

The combination of the host organisms and the vectors appropriate for the organisms, such as plasmids, viruses or phages, such as, for example, plasmids with the RNA polymerase/promoter system, phages λ, μ or other temperate phages or transposons and/or other advantageous regulatory sequences forms an expression system. The term "expression system" means, for example, a combination of mammalian cells such as CHO cells, and vectors, such as pcDNA3neo vector, which are suitable for mammalian cells.

As described above, the gene product can also be expressed advantageously in transgenic animals, for example mice, sheep, or transgenic plants. It is likewise possible to program cell-free translation systems with the RNA derived from the nucleic acid.

The invention furthermore provides a process for preparing a monooxygenase according to the invention, which comprises cultivating a monooxygenase-producing microorganism, if appropriate inducing the expression of the monooxygenase, and isolating the monooxygenase from the culture. If desired, the monooxygenase according to the invention can thus also be produced on an industrial scale.

The microorganism can be cultivated and fermented by known methods. Bacteria, for example, can be grown in a TB or LB medium and at 20-40° C. and a pH of 6-9. Suitable cultivation conditions are described in detail in T. Maniatis, E. F. Fritsch and J. Sambrook, Molecular Cloning: A Laboratory Manual, Cold Spring Harbor Laboratory, Cold Spring Harbor, N.Y. (1989), for example.

If the monooxygenase is not secreted into the culture medium, the cells are then lyzed and the monooxygenase is obtained from the lysate using known methods for the isolation of proteins. The cells can be lyzed alternatively by high-frequency ultrasound, by high pressure, for example in a French pressure cell, by osmolysis, by the action of detergents, lytic enzymes or organic solvents, by homogenization or by a combination of a plurality of the processes mentioned. Purification of the monooxygenase can be achieved by known chromatographic processes, such as molecular sieve chromatography (gel filtration), such as Q-Sepharose chromatography, ion-exchange chromatography and hydrophobic chromatography, and by other customary processes, such as ultrafiltration, crystallization, salting out, dialysis and native gel electrophoresis. Suitable processes are described, for example, in Cooper, F. G., Biochemische Arbeitsmethoden [Biochemical Procedures], Verlag Walter de Gruyter, Berlin, N.Y. or in Scopes, R., Protein Purification, Springer Verlag, New York, Heidelberg, Berlin.

To isolate the recombinant protein, it is particularly advantageous to use vector systems or oligonucleotides which extend the cDNA by certain nucleotide sequences and thus code for modified polypeptides or fusion proteins which serve to simplify purification. Suitable modifications of this type are, for example, so-called "tags" which act as anchors, such as, for example, the modification known as hexa-histidine anchor, or epitopes which can be recognized as antigens by antibodies (described, for example, in Harlow, E. and Lane, D., 1988, Antibodies: A Laboratory Manual. Cold Spring Harbor (N.Y.) Press). These anchors can be used to attach the proteins to a solid support such as, for example, a polymer matrix, which can, for example, be packed into a chromatography column, or to a microtiter plate or to another support.

These anchors can also at the same time be used to recognize the proteins. It is also possible to use for recognition of the proteins conventional markers such as fluorescent dyes, enzyme markers which form a detectable reaction product after reaction with a substrate, or radioactive markers, alone or in combination with the anchors for derivatizing the proteins.

The invention moreover relates to a process for the microbiological oxidation of organic compounds, for example N-heterocyclic mono-, bi- or polynuclear aromatic compounds according to the above definition, which comprises a1) culturing a recombinant microorganism according to the above definition in a culture medium, in the presence of an exogenous (added) substrate or an intermediately formed substrate, which substrate is oxidizable by the monooxygenase according to the invention, preferably in the presence of oxygen (i.e. aerobically); or a2) incubating a substrate-containing reaction medium with an enzyme according to the invention, preferably in the presence of oxygen and an electron donor; and b) isolating the oxidation product formed or a secondary product thereof from the medium.

The oxygen required for the reaction either passes from the atmosphere into the reaction medium or, if required, can be added in a manner known per se.

The oxidizable substrate is preferably selected from a) unsubstituted or substituted N-heterocyclic mono-, bi- or polynuclear aromatic compounds;

b) unsubstituted or substituted mono- or polynuclear aromatics;

c) straight-chain or branched alkanes and alkenes;

d) unsubstituted or substituted cycloalkanes and cycloalkenes.

A preferred process variant is directed to the formation of indigo/indirubin and is characterized by the fact that the substrate is indole formed as an intermediate in the culture and that the indigo and/or indirubin formed in the culture medium is isolated by oxidation of hydroxyindole intermediates.

If the oxidation according to the invention is carried out using a recombinant microorganism, the culturing of the microorganisms is preferably first carried out in the presence of oxygen and in a complex medium, such as, for example, TB or LB medium at a culturing temperature of approximately 20 to 40° C. and a pH of approximately 6 to 9, until an adequate cell density is reached. The addition of exogenous indole is usually not necessary, as this is intermediately formed by the microorganism. However, when using other substrates, addition of exogenous substrate may be required. In order to be able to control the oxidation reaction better, the use of an inducible, in particular temperature-inducible, promoter is preferred. The temperature is in this case increased to the necessary induction temperature, e.g. 42° C. in the case of the $P_rP_1$ promoter, this is maintained for a sufficient period of time, e.g. 1 to 10 or 5 to 6 hours, for the expression of the monooxygenase activity and the temperature is then reduced again to a value of approximately 30 to 40° C. The culturing is then continued in the presence of oxygen for 12 hours to 3 days. The pH can, in particular in the case of indole oxidation, be increased by addition of NaOH, e.g. to 9 to 10, whereby the indigo formation or indirubin formation is additionally promoted by atmospheric oxidation of the enzymatically formed oxidation products 2- and 3-hydroxyindole.

The indigo/indirubin formation according to the invention is illustrated by the reaction scheme below:

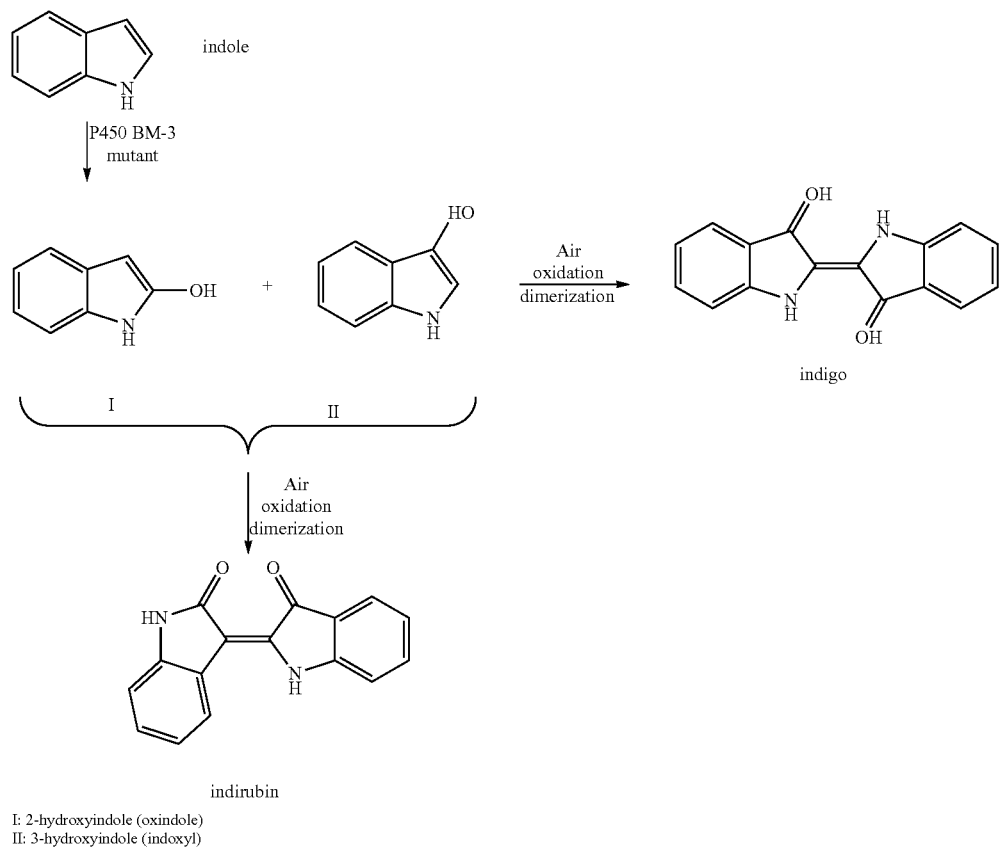

I: 2-hydroxyindole (oxindole)
II: 3-hydroxyindole (indoxyl)

However, if the oxidation according to the invention is carried out using purified or enriched enzyme mutants, the enzyme according to the invention is dissolved in an exogenous substrate-containing, for example indole-containing medium (approximately 0.01 to 10 mM, or 0.05 to 5 mM), and the reaction is carried out, preferably in the presence of oxygen, at a temperature of approximately 10 to 50° C., such as, for example, 30 to 40° C., and a pH of approximately 6 to 9 (such as established, for example, using 100 to 200 mM phosphate or tris buffer), and in the presence of a reductant, the substrate-containing medium moreover containing, relative to the substrate to be oxidized, an approximately 1- to 100-fold or 10- to 100-fold molar excess of reduction equivalents. The preferred reductant is NADPH. If required, the reducing agent can be added in portions.

In a similar manner, the oxidizable substrates which are preferably used are: n-hexane, n-octane, n-decane, n-dodecane, cumene, 1-methylindole, 5-Cl- or Br-indole, indene, benzothiophene, α-, β- and γ-ionone, acridine, naphthalene, 6-methyl- or 8-methylquinoline, quinoline and quinaldine.

The enzymatic oxidation reaction according to the invention can be carried out, for example, under the following conditions:

| | |
|---|---|
| Substrate concentration: | from 0.01 to 20 mM |
| Enzyme concentration: | from 0.1 to 10 mg/ml |
| Reaction temperature: | from 10 to 50° C. |
| pH: | from 6 to 8 |
| Buffer: | from 0.05 to 0.2 M potassium phosphate, or Tris/HCl |
| Electron donor: | is preferably added in portions (initial concentration about 0.1 to 2 mg/ml) |

The mixture can briefly (from 1 to 5 minutes) be preincubated (at about 20-40° C.) before the reaction is initiated, for example by adding the electron donors (e.g. NADPH). The reaction is carried out aerobically, if appropriate with additional introduction of oxygen.

In the substrate oxidation process according to the invention, oxygen which is present in or added to the reaction medium is cleaved reductively by the enzyme. The required reduction equivalents are provided by the added reducing agent (electron donor).

The oxidation product formed can then be separated off from the medium and purified in a conventional manner, such as, for example, by extraction or chromatography.

Further subjects of the invention relate to bioreactors, comprising an enzyme according to the invention or a recombinant microorganism according to the invention in immobilized form.

A last subject of the invention relates to the use of a cytochrome P450 monooxygenase according to the invention or of a vector or microorganism according to the invention for the microbiological oxidation of a substrate from one of the groups a) to d), in particular of N-heterocyclic mono-, bi- or polynuclear aromatic compounds, and preferably for the formation of indigo and/or indirubin.

The present invention is now described in greater detail with reference to the following examples.

EXAMPLE 1

Randomization of Specific Codons of P450 BM-3

The experiments were carried out essentially as described in (19). Three positions (Phe87, Leu188 and Ala74) were randomized with the aid of site-specific mutagenesis using the Stratagene QuikChange kit (La Jolla, Calif., USA). The following PCR primers were used for the individual positions:

Phe87: 5'-gcaggagacgggttgnnnacaagctggacg-3' (SEQ ID NO:3),

5'-cgtccagcttgtnnncaacccgtctcctgc-3', (SEQ ID NO:4)

Leu188: 5'-gaagcaatgaacaagnnncagcgagcaaatccag-3' (SEQ ID NO:5),

5'-ctggatttgctcgctgnnncttgttcattgcttc-3' (SEQ ID NO:6);

Ala74: 5'-gctttgataaaaacttaaagtcaannncttaaatttgtacg-3' (SEQ ID: NO:7),

5'-cgtacaaatttaagnnnttgacttaagtttttatcaaagc-3' (SEQ ID NO:8)

The conditions for the PCR were identical for all three positions. In particular, 17.5 µmol of one of each primer, 20 pmol of template plasmid DNA, 3 U of the Pfu polymerase and 3.25 nmol of each dNTP were used per 50 µl reaction volume. The PCR reaction was started at 94° C./1 min and the following temperature cycle was then carried out 20 times: 94° C., 1 min; 46° C., 2.5 min; 72° C., 17 min. After 20 cycles, the reaction was continued at 72° C. for 15 min. After the PCR, the template DNA was digested at 37° C. for 3 h using 20 U of DpnI. E. coli DH5a was then transformed. The transformed E. coli DH5a cells were plated out onto LB agar plates which contained 150 µg/ml of ampicillin. Incubation was then carried out at 37° C. for 18 h.

EXAMPLE 2

Expression and Purification of the P450 BM-3 and its Mutants and Production of a Blue Pigment The P450 BM-3 gene and the mutants thereof were expressed under the control of the strong, temperature-inducible $P_R P_L$ promoter of the plasmid pCYTEXP1 in E. coli DH5α as already described (20). Colonies were picked up using sterile toothpicks and transferred to microtiter plates having 96 hollows, comprising 200 µl of TB medium and 100 µg/ml of ampicillin per hollow. Incubation was then carried out at 37° C. overnight. 40 µl of the cell culture of one of each hollow were then transferred to a culture tube which contained 2 ml of TB medium with 100 µg/ml of ampicillin. Culturing was then carried out at 37° C. for 2 h. The temperature was then increased to 42° C. for 6 h for induction. Culturing was then continued at 37° C. overnight, a blue pigment being produced.

The preparative production of enzyme or blue pigment was carried out starting from a 300 ml cell culture ($OD_{578nm}$=0.8 to 1.0). For the isolation of the enzyme, the cells were centrifuged off at 4000 rpm for 10 min and resuspended in 0.1 M $K_xPO_4$ buffer, pH 7.4. The ice-cooled cells were carefully disrupted with the aid of a Branson sonifer W25 (Dietzenbach, Germany) at an energy output of 80 W by 2 min sonification three times. The suspensions were centrifuged at 32570×g for 20 min. The crude extract was employed for the activity determination or for the enzyme purification. The enzyme purification was carried out as already described in (21), to which reference is expressly made hereby. The concentration of purified enzyme was determined by means of the extinction difference at 450 and 490 nm, as already described in (11), using an extinction coefficient ε of 91 $mM^{-1} cm^{-1}$.

EXAMPLE 3

Isolation of Mutants which Produce Large Amounts of Blue Pigment 100 colonies in each case were isolated from the mutants of one of each position, which were produced by randomized mutagenesis of the codon of the corresponding position. These colonies were cultured in culture tubes for the production of blue pigment.

After washing the cells with water and a number of slow centrifugation steps (500 rpm), the blue pigment was extracted using dimethyl sulfoxide (DMSO). The solubility of the blue pigment was greatest in DMSO. The absorption of the extract was determined at 677 nm. That mutant which produced the largest amount of blue pigment, especially mutants from a specific position, was used for DNA sequencing (ABI DNA sequencing kit; ABI Prism™ 377 DNA sequencer) and moreover as a template for site-specific randomized mutagenesis.

EXAMPLE 4

Activity Test for the Indole Hydroxylation

The indole hydroxylation activity was tested in a solution which contained 8 µl of a 10-500 mM indole solution in DMSO, 850 µl of tris/HCl buffer (0.1 M, pH 8.2) and 0.6 nmol of P450 BM-3 wild type or mutant in a final volume of 1 ml. The mixture was preincubated for 9 min before the reaction was started by addition of 50 µl of an aqueous 1 mM solution of NADPH. The reaction was stopped after 20 sec by addition of 60 µl of 1.2 M KOH. Within 5 to 30 sec (under aerobic conditions), the enzyme products were converted completely into indigo [$\Delta^{2,2'}$-biindoline]-3,3'-dione) and indirubin ([$\Delta^{2,3'}$-biindoline]-2',3-dione). The indigo production was determined by means of its absorption at 670 nm. A calibration curve using pure indigo showed an extinction coefficient of 3.9 $mM^{-1} cm^{-1}$ at this wavelength. A linear curve was obtained for indigo production in a reaction time of 40 sec using 0.6 nmol of wild type or P450 BM-3 mutant and 0.05 to 5.0 mM of indole. Indirubin shows a very weak absorption at 670 nm and the amount of indirubin formed was very much smaller than the amount of indigo formed. The formation of indirubin was neglected in the determination of the kinetic parameters. The NADPH consumption was determined at 340 nm and calculated as described (17) using an extinction coefficient of 6.2 $mM^{-1} cm^{-1}$.

EXAMPLE 5

Purification of Indigo and Indirubin

After washing the cells with water and repeated centrifugation at 500 g, the blue pellet formed was extracted using tetrahydrofuran (THF). The extract was evaporated almost to dryness and the red pigment was extracted a number of times with 50 ml of absolute ethanol. The residual blue solid was dissolved in THF and analyzed by thin-layer chromatography (TLC). The ethanol solution was evaporated and purified by silica gel chromatography (TLC 60, Merck, Darmstadt, Germany; 2 cm×30 cm) before it was washed with THF and petroleum ether in a ratio of 1:2. The red solution obtained was evaporated and its purity was determined by TLC. The absorption spectra of the blue and of the red pigment were determined in a range from 400 to 800 nm with the aid of an Ultraspec 3000 spectrophotometer (Pharmacia, Uppsala, Sweden). The blue and the red color were moreover analyzed by mass spectrometry and $^1$H-NMR spectroscopy.

EXPERIMENTAL RESULTS

1. Increasing the Productivity for Blue Pigment by P450 BM-3 Mutagenesis

Native P450 BM-3 does not have the ability to produce the blue indigo-containing pigment, or the precursor substances 2- or 3-hydroxyindole. In order to be able to prepare a sufficient amount of blue pigment, P450 BM-3 was subjected to evolution in a controlled manner. All mutants which produced the blue pigment were sequenced. It was found that at least one of the following three positions were mutated: Phe87, Leu188 and Ala74. It was therefore assumed that these three positions play a crucial role for the activity of P450 BM-3 in the production of blue pigment. From the structure of the heme domain of cytochrome P450 BM-3, complexed with palmitoleic acid, it is seen that Phe87 prevents the substrate from coming closer to the heme group (14). The mutant Phe87Val shows a high regio- and stereoselectivity in the epoxidation of (14S,15R)-arachidonic acid (13) and the mutant Phe87Ala shifts the hydroxylation position of $\omega$-1, $\omega$-2 and $\omega$-3 to $\omega$ (22). The position 87 was therefore selected as first for the site-specific randomized mutagenesis with the aid of PCR. In tube cultures, 7 colonies were obtained which produced a small amount of blue pigment after induction. The colony which produced the largest amount of the blue pigment was selected for the DNA sequencing. The sequence data showed substitution of Phe87 by Val. The mutant Phe87Val was then used as a template for the second round of site-specific randomized mutagenesis on position Leu188. The structure of the heme domain, complexed with palmitoleic acid, shows that the repositioning of the F and G helices brings the residue Leu188 into direct contact with the substrate (14). This position can therefore play an important role in substrate binding or orientation. After the second screening passage, 31 colonies were observed which produced the blue pigment. The mutant which produced the largest amount of pigment contained the substitutions Phe87Val and Leu188Gln. This mutant was then mutated in position Ala74 in the third passage of site-specific randomized mutagenesis. In this case the triple mutant F87L188A74 (Phe87Val, Leu188Gln and Ala74Gly) was obtained, which produced several mg of blue pigment in a 2-liter flask, containing 300 ml of TB medium. This amount was sufficient for the isolation and characterization of the blue pigment.

2. Isolation and Identification of the Blue Pigment

After washing the cells, the residual blue pellet was extracted with THF and analyzed by TLC. The blue pigment was separated into a rapidly migrating blue component and into a more slowly migrating red component. Both components showed exactly the same mobility parameters as the components of a commercial indigo sample.

After the purification, the absorption spectra of both components were determined in DMSO. The blue component showed the same spectrum as a commercial indigo sample. The purified blue and red components were each analyzed by mass spectrometry. The mass spectra of both pigments showed a strong molecular ion peak at m/e=262 and two fragment peaks at m/e=234 and 205 (relative intensity in each case 10%). This pattern is typical of indigoid compounds. The elementary composition of these ions was determined by high-resolution mass spectrometry as $C_{16}H_{10}N_2O_2$, $C_{15}H_{10}N_2O$ and $C_{14}H_9N_2$. This is also characteristic of structures of the indigo type. The blue pigment was thus identified as indigo and the red pigment as indirubin. For the confirmation of the structure, 500 MHz $^1$H-NMR spectra of both pigments were carried out in DMSO-$D_6$ solution. The results agreed with the literature data (23).

3. Production of Indigo Using Isolated Enzymes

It is known that indigo is accessible from indole by microbial transformation (24-26). None of these microbial systems, however, contained a P450 monooxygenase. According to the invention, the catalytic activity of the pure enzyme for indole was first determined. The mutant F87L188A74 was mixed with indole. No color reaction could be observed. Only after addition of NADPH to the reaction mixture was the blue pigment formed after approximately 20 min. By adjustment of the pH of the reaction mixture to a value of approximately 11, 30 sec after addition of NADPH, the blue coloration was visible within a few seconds. Control experiments using native P450 BM-3 were always negative, even using increased concentrations of enzyme, indole and NADPH. The blue pigment was extracted using ethyl acetate and analyzed by TLC. The blue pigment again separated into a more rapidly running blue component and into a slower running red component. The Rf values and the absorption spectra were identical to those values of the extracts from the fermentation broth. The F87L188A74 mutant of P450 BM-3 is thus an indole hydroxylase.

Two routes have previously been described for the enzymatic transformation of indole to indigo. One route is catalyzed by a dioxygenase, the other by a styrene monooxygenase (24, 25). The NADPH stoichiometry is in both cases 2. It was therefore assumed that in contrast to the dioxygenases the mutant F87L188A74 according to the invention hydroxylates indole in only one position to form oxindole (2-hydroxyindole) or indoxyl (3-hydroxyindole).

4. Kinetic Parameters of Indole Hydroxylation

Pure samples of the wild-type enzyme P450 BM-3 and of the mutants Leu188Gln, Phe87Val, F87L188 and F87L188A74 were used for the determination of the kinetic parameters of indole hydroxylation. The results are summarized in Table 1 below.

TABLE 1

Kinetic parameters of the P450 BM-3 mutants for indole hydroxylation

| Mutants | $K_{cat}(S^{-1})$ | $K_m$ (mM) | $K_{cat}/K_m$ $(M^{-1}s^{-1})$ |
|---|---|---|---|
| WT | —[a] | — | — |
| Leu188Gln | n.d.[b] | n.d. | n.d. |
| Phe87Val | 2.03 (0.14) | 17.0 (1.0) | 119 |
| F87L188 | 2.28 (0.16) | 4.2 (0.4) | 543 |
| F87L188A74 | 2.73 (0.16) | 2.0 (0.2) | 1365 |

[a]no activity was observed;
[b]not determined (activity was too low to be measured)

Even with an excess of purified enzyme and high indole concentration, the wild-type enzyme is not able to oxidize indole. The mutant Leu188Gln shows a low activity. The mutant Phe87Val shows a catalytic activity of 119 $M^{-1}s^{-1}$ for indole hydroxylation. The catalytic efficiency of the double mutant F87L188 (Phe87Val,Leu188Gln) increased to 543 $M^{-1}s^{-1}$ and was increased to 1365 $M^{-1}s^{-1}$ by introduction of the further substitution Ala74Gly. The $K_{cat}$ values increased from Phe87Val to the triple mutant by a total of 35%, while the $K_m$ values decreased approximately by seven-fold. This indicates that Ala74Gly and Leu188Gln are mainly involved in substrate binding.

For the triple mutant F87L188A74, the indole turnover rate ($K_{cat}$=2.73 $s^{-1}$) was more than ten times higher than for most P450 enzymes (18).

EXAMPLE 6

Hydroxylation of N-Octane Using Modified Cytochrome P450 Monooxygenase

The reactions were carried out using a P450 BM-3 monooxygenase mutant comprising the following mutations: Phe87Val Leu188Gln Ala74Gly The chosen substrate was n-octane. For the hydroxylation of n-octane, the following aerobic reaction mixture was used:

| P450 BM-3 mutant: | 17.5 mg (lyophilisate) |
|---|---|
| Reaction buffer: | 9.1 ml (potassium phosphate buffer 50 mM, pH 7.5) |
| Substrate: | 50 µl of a 60 mM solution (in acetone) |
| Temperature: | 25° C. |

The enzyme lyophilisate was dissolved in 500 µl of reaction buffer and initially incubated at room temperature with substrate and reaction buffer for 5 minutes. 300 µl NADPH solution (5 mg/ml) were then added. Addition of NADPH was repeated two more times. The progress of the reaction was monitored by measuring the absorption at 340 nm, which allows the NADPH decrease to be observed. NADPH is added in aliquots of 300 µl, since too high a concentration of NADPH in the reaction solution would result in inactivation of the enzyme. To isolate the products, the reaction solution was then extracted three times with 5 ml of diethyl ether. The combined organic phases were dried over $MgSO_4$ and concentrated. The products were then characterized by TLC, GC/MS and NMR.

The GC/MS analysis of the reaction mixture gave the following result:

| Compound | Rt [min][1] | Conversion [%] |
|---|---|---|
| 4-octanol | 13.51 | 37 |
| 3-octanol | 14.08 | 47 |
| 2-octanol | 14.26 | 16 |

[1]Temperature program: 40° C. 1 min isothermic/3° C./min 95° C./10° C./min 275° C.; apparatus: Finnigan MAT 95; GC: HP 5890 Series II Split Injector; Column: HP-5MS (methylsiloxane) 30 m x 0.25 mm; Carrier gas: 0.065 ml of He/min No starting material was found.

EXAMPLE 7

Hydroxylation of Aromatics, Heteroaromatics and Trimethylcyclo-Hexenyl Compounds a) Example 6 was repeated, but using, instead of n-octane, the substrate naphthalene. The products that were identified were 1-naphthol and cis-1,2-dihydroxy-1,2-dihydronaphthalene. 88% of the naphthalene starting material had been converted.

Analytic methods for reactions with naphthalene
GC:
Apparatus: Carlo Erba Strumentazion Typ HRGC 4160 on Column Injector; Column: DB5 30m×0.2 mm; Material: 5% diphenyl-95% dimethylpolysiloxane; Carrier gas: 0.5 bar $H_2$;
Temperature program: 40° C. 1 min isothermic/10° C./min to 300° C. Rt(1-naphthol)=16.68
NMR:
1-Naphthol and cis-1,2-dihydroxy-1,2-dihydro-naphthalene were identified in the $^1H$ NMR.

b) Example 6 was repeated but using, instead of n-octane, the substrate 8-methylquinoline. 5-Hydroxy-8-methylquinoline was identified as main product, in addition to other derivatives (product ratio 5:1). 35% of the starting material used had been converted.

c) Example 6 was repeated but using, instead of n-octane, the substrate α-ionone. 3-Hydroxy-α-ionone was identified as main product, in addition to other derivatives (product ratio: 76:24). 60% of the starting material used had been converted.

d) Example 6 was repeated, but using, instead of n-octane, the substrate cumene (isopropylbenzene). Five monohydroxy products and one dihydroxy product were identified. 70% of the starting material used had been converted.

REFERENCES

1. Yano, T., Oue, S., and Kagamiyama, H. (1998) Proc. Natl. Acad. Sci. USA 95, 5511-5515.
2. Zhang, J.-H., Dawes, G., and Stemmer, W. P. C. (1997) Proc. Natl. Acad Sci. USA 94, 4504-4509.
3. Wan, L., Twitchett, M. B., Eltis, L. D., Mauk, A. G., and Smith, M. (1998) Proc. Natl. Acad Sci USA 95, 12825-12831.
4. Cronin, C. N. (1998) J. Biol. Chem 273, 24465-24469.
5. Wilks, H. M., Hart, K. W., Feeney, R., Dunn, C. R., Muirhead, H., Chia, W. N., Barstow, D. A., Atkinson, T., Clarke, A. R., Holbrook, I J. (1988) Science 242, 1541-1544.
6. Hedstrom, L., Szilagyi, L., Rutter, W. J. (1992) Science 255, 1249-1253.
7. Tucker, C. L., Hurley, J. H., Miller, T. R., and Hurley, I B. (1998) Proc. Natl. Acad. Sci. USA 95, 5993-5997.
8. Quemeneur, E., Moutiez, J.-B. C., and Menez, A. (1998) Nature (London) 391, 301-303.
9. Marsden, A-F. A., Wilkinson, B., Cortes, J., Dunster, N. J., Staunton, I Leadlay, P. F. (1998) Science 279, 199-201.
10. Chen, R., Greer, A., and Dean, A. M. (1998) Proc. Natl. Acad. Sci. US4 95, 11666-11670.
11. Boddupalli, S. S., Estabrook, R. W. and Peterson, J. A. (1990) J Biol. Chem 265, 4233-4239.
12. Capdevila, J. H., Wie, S., Helvig, C., Falck, J. R., Belosludtsev, Y., Truan, G., Graham-Lorence, S. E., and Peterson, J. A. (1996) J. Biol. Chem 271, 22663-22671.
13. Graham-Lorence, S., Truan, G., Peterson, J. A., Flack, J. R., WeL S., Helvig, C., Capdevilla, J. H. (1997) J. Biol. Chem 272, 1127-1135.
14. Li, H., Poulos, T. L. (1997) Nat. Structural Biol., 4, 140-146.
15. Ravichandran, K G., Sekhar, S., Boddupalli, S., Hasemann, C. A., Peterson, J. A., Deisenhofer, 1 (1993) Science 261, 731-736.
16. Modi S., Sutcliffe, M. J., Primrose, W. U., Lian, L.-Y., Roberts, G. C. K (1996) Nat. Structural Biol. 3, 414-417.

17. Oliver, C. F., ModL S., Primrose, W. U., Lian, L. Y. and Roberts, G. C. K (1997) Biochem. J. 327, 537-544.
18. Guengerich, F. G. (1991) J. Biol. Chem 266, 10019-10022.
19. Cherry, J. R., Lamsa, M. H., Schneider, P., Vind, J., Svendsen, A-., Jones, A., and Pedersen, A. H. (1999) Nature Biotechnology 17, 379-384.
20. Schwaneberg, U., Schmidt-Dannert, C., Schmitt, J., and Schmid, R. D. (1999) Anal. Biochem. 269, 359-366.
21. Schwaneberg, U, Sprauer, A L, Schmidt-Dannert, C., and Schmid, R. D. J of Chromatogr. A, in press.
22. Oliver, C. F., Modi, S., Sutcliffe, M. J., Primrose, W. U., Lian, L. Y. and Roberts, G. C. K (1997) Biochemistry 36, 1567-1572.
23. Hart, S., Koch, K R., and Woods, D. R. (1992) J Gen. Microbiol. 138, 211-216
24. Murdock, D., Ensley, B. D., Serdar, C. and Thalen, M. (1993) Bio/Technology 11, 381-385.
25. O'Connor, ICE., Dobson, A-W. and Hartmans, S. (1997) Appl. Environ. Microbiol. 63, 4287-4291.
26. Eaton, R. W. and Chapman, P. J. (1995) J Bacteriol. 177, 6983-6988.

---

The invention claimed is:

1. A process for the microbiological oxidation of a substrate compound having an N-, O- or S-heterocyclic mono- or polynuclear aromatic moiety,
which process comprises oxidizing at least one aromatic C—H group of the heterocyclic aromatic moiety by
   a1) culturing a recombinant microorganism which expresses a cytochrome P450 monooxygenase of bacterial origin in a culture medium, in the presence of an exogenous or intermediately formed substrate; or
   a2) incubating a substrate-containing reaction medium with a cytochrome P450 monooxygenase of bacterial origin; and
   b) isolating the oxidation product formed or a secondary product thereof from the medium, and
wherein the monooxygenase is derived from cytochrome P450 monooxygenase BM-3 from *Bacillus megaterium* having the amino acid sequence according to SEQ ID NO:2 by a mutation,
and the mutation consists of a functional mutation in one, two or all of sequence positions 74, 87 and 188, whereby
Phe87 is replaced by Ala, Val or Leu,
Leu188 is replaced by Asn or Gln, and/or
Ala74 is replaced by Val or Gly.

2. The process as claimed in claim 1, wherein the exogenous or intermediately formed substrate of claim 1, alternative a1), or the substrate contained in the reaction medium of claim 1, alternative a2) is selected from optionally substituted N-, O- or S-heterocyclic mono- or polynuclear aromatic compounds.

3. The process as claimed in claim 1, where the mutant has one of the following mono- or polyamino acid substitutions:
   a) Phe87Val;
   b) Phe87Val and Leu188Gln;
   c) Phe87Val, and Leu188Gln, and Ala74Gly.

4. The process as claimed in claim 1, wherein the exogenous substrate is at least one compound selected from unsubstituted or substituted N-, O- or S-heterocyclic mono- or polynuclear aromatic compounds, the exogenous substrate is added to a medium and the oxidation is carried out by enzymatic reaction of the substrate-containing medium in the presence of oxygen at a temperature of approximately 20 to 40° C. and a pH of approximately 6 to 9, where the substrate-containing medium additionally contains an approximately 10- to 100-fold molar excess of reduction equivalents based on the substrate.

5. The process as claimed in claim 4, wherein the exogenous substrate is a compound selected from indole, 1-methylindole, acridine, 6-methyl- or 8-methylquinoline, quinoline and quinaldine.

6. The process for the microbiological production of indigo and/or indirubin, which comprises
   a1) culturing a recombinant microorganism which produces an indole-oxidizing cytochrome P450 monooxygenase in a culture medium, in the presence of exogenous or intermediately formed indole; or
   a2) incubating an indole-containing reaction medium with an indole-oxidizing cytochrome P450 monooxygenase; and
   b) isolating the oxidation product formed or a secondary product thereof from the medium,
wherein the monooxygenase is derived from cytochrome P450 monooxygenase BM-3 from *Bacillus megaterium* having the amino acid sequence according to SEQ ID NO: 2 by a mutation,
and the mutation consists of a functional mutation in one, two or all of sequence positions 74, 87 and 188, whereby
Phe87 is replaced by Ala, Val or Leu,
Leu188 is replaced by Asn or Gln, and/or
Ala74 is replaced by Val or Gly.

7. The process as claimed in claim 6, wherein the indigo and/or indirubin obtained, which was produced by oxidation of intermediately formed indole, is isolated from the medium.

8. The process as claimed in claim 7, wherein the indole oxidation is carried out by culturing the microorganisms in the presence of oxygen at a culturing temperature of approximately 20 to 40° C. and a pH of approximately 6 to 9.

9. The process as claimed in claim 8, where the monooxygenase has at least one of the following mono- or polyamino acid substitutions:
   a) Phe87Val;
   b) Phe87Val, Leu188Gln; or
   c) Phe87Val, Leu188Gln, Ala74Gly.

10. The process as claimed in claim 1, wherein the functional mutation occurs in the amino acid sequence position 87, or in the positions 87 and 188, or in the positions 87, 188 and 74, whereby
Phe87 is replaced by Ala, Val or Leu,
Leu188 is replaced by Asn or Gln, and
Ala74 is replaced by Val or Gly.

11. The process as claimed in claim 6, wherein the functional mutation occurs in the amino acid sequence position 87, or in the positions 87 and 188, or in the positions 87, 188 and 74, whereby
Phe87 is replaced by Ala, Val or Leu,
Leu188 is replaced by Asn or Gln, and
Ala74 is replaced by Val or Gly.

* * * * *